(12) United States Patent
Brugger et al.

(10) Patent No.: US 12,121,643 B2
(45) Date of Patent: Oct. 22, 2024

(54) FLOW REVERSING DEVICE

(71) Applicant: NxStage Medical, Inc., Lawrence, MA (US)

(72) Inventors: James M. Brugger, Newburyport, MA (US); William J. Schnell, Libertyville, IL (US); Kenneth E. Buckler, Methuen, MA (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 17/889,963

(22) Filed: Aug. 17, 2022

(65) Prior Publication Data

US 2022/0387687 A1     Dec. 8, 2022

Related U.S. Application Data

(63) Continuation of application No. 16/493,563, filed as application No. PCT/US2018/024389 on Mar. 26, 2018, now Pat. No. 11,426,504.

(Continued)

(51) Int. Cl.
    *A61M 1/36*          (2006.01)
    *A61M 39/22*      (2006.01)
    (Continued)

(52) U.S. Cl.
    CPC .......... *A61M 1/367* (2013.01); *A61M 39/223* (2013.01); *F16K 11/0525* (2013.01);
    (Continued)

(58) Field of Classification Search
    CPC ................ A61M 1/367; A61M 39/223; A61M 2039/229; F16K 11/0525; F16K 11/0853; F16K 11/027
    See application file for complete search history.

(56) References Cited

U.S. PATENT DOCUMENTS

| | | | | |
|---|---|---|---|---|
| 579,432 A | * | 3/1897 | Harrison | ................ B62D 5/083 |
| | | | | 251/188 |
| 715,266 A | * | 12/1902 | Heston | .................. B62D 5/083 |
| | | | | 137/625.23 |

(Continued)

FOREIGN PATENT DOCUMENTS

| | | |
|---|---|---|
| CN | 104755132 A | 7/2015 |
| JP | 2007510471 A | 4/2007 |
| WO | 2005046439 A2 | 5/2005 |

OTHER PUBLICATIONS

International Preliminary Report on Patentability mailed Jul. 10, 2019 for International Patent Application No. PCT/US2018/024389.

(Continued)

*Primary Examiner* — Michael R Reid
(74) *Attorney, Agent, or Firm* — Potomac Law Group, PLLC

(57) ABSTRACT

A flow switch device includes a flow switch with four ports oriented at 90 degree intervals around a center of the flow switch. The flow switch is of a type that forms selectable flow passages between ports separated by 90 degrees and blocks flow between ports separated by 180 degrees in each of multiple selected positions. Two of the ports are connected to fixed flow passages and each of the fixed flow passages defines a flow path toward a remote port separated from each of the fixed flow passages by 180 degrees so that each of the fixed flow passages and a respective remote port are positioned in pairs on opposite sides of the flow switch.

8 Claims, 10 Drawing Sheets

Related U.S. Application Data

(60) Provisional application No. 62/478,518, filed on Mar. 29, 2017.

(51) Int. Cl.
*F16K 11/052* (2006.01)
*F16K 11/085* (2006.01)
*F16K 35/04* (2006.01)

(52) U.S. Cl.
CPC .......... *F16K 11/0853* (2013.01); *F16K 35/04* (2013.01); *A61M 2039/229* (2013.01)

(56) References Cited

U.S. PATENT DOCUMENTS

| | | | |
|---|---|---|---|
| 3,973,592 A | 8/1976 | Cleaver et al. | |
| 4,506,703 A | 3/1985 | Baron | |
| 4,653,537 A | 3/1987 | Voith | |
| 5,839,470 A * | 11/1998 | Hiejima | A61M 5/16877 137/599.08 |
| 6,177,049 B1 | 1/2001 | Schnell et al. | |
| 6,743,193 B2 | 6/2004 | Brugger et al. | |
| 7,815,588 B2 * | 10/2010 | Sakiewicz | A61M 1/3656 251/231 |
| 8,002,727 B2 * | 8/2011 | Brugger | A61M 1/3656 137/625.42 |
| 9,415,151 B2 | 8/2016 | Schlaeper et al. | |
| 9,486,569 B2 * | 11/2016 | Eikelmann | A61M 1/367 |
| 9,803,760 B2 * | 10/2017 | Morein | F16K 11/0853 |
| 2003/0138348 A1 | 7/2003 | Bell et al. | |
| 2008/0214979 A1 | 9/2008 | Brugger et al. | |
| 2013/0110028 A1 | 5/2013 | Bachmann et al. | |
| 2014/0088482 A1 | 3/2014 | Schlaeper et al. | |
| 2017/0021083 A1 * | 1/2017 | Gray | G01L 19/0084 |

OTHER PUBLICATIONS

International Search Report and Written Opinion mailed Aug. 16, 2018 for International Patent Application No. PCT/US2018/024389.
Invitation to Pay Additional Fees with Partial International Search and Provisional Opinion mailed Jun. 21, 2018 for International Patent Application No. PCT/US2018/024389.
Office Action (Notice of Reasons for Refusal) mailed Nov. 17, 2020 for Japanese Patent Application No. 2019-553021.
Written Opinion of the International Preliminary Examining Authority mailed Feb. 20, 2019 for International Patent Application No. PCT/US2018/024389.

* cited by examiner

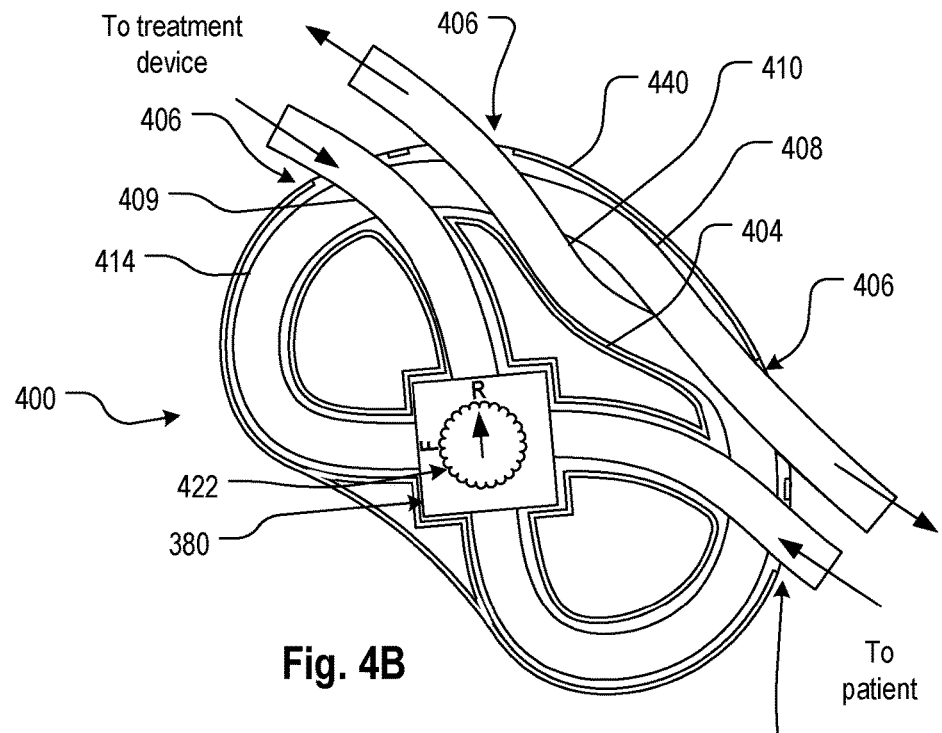
Fig. 4B
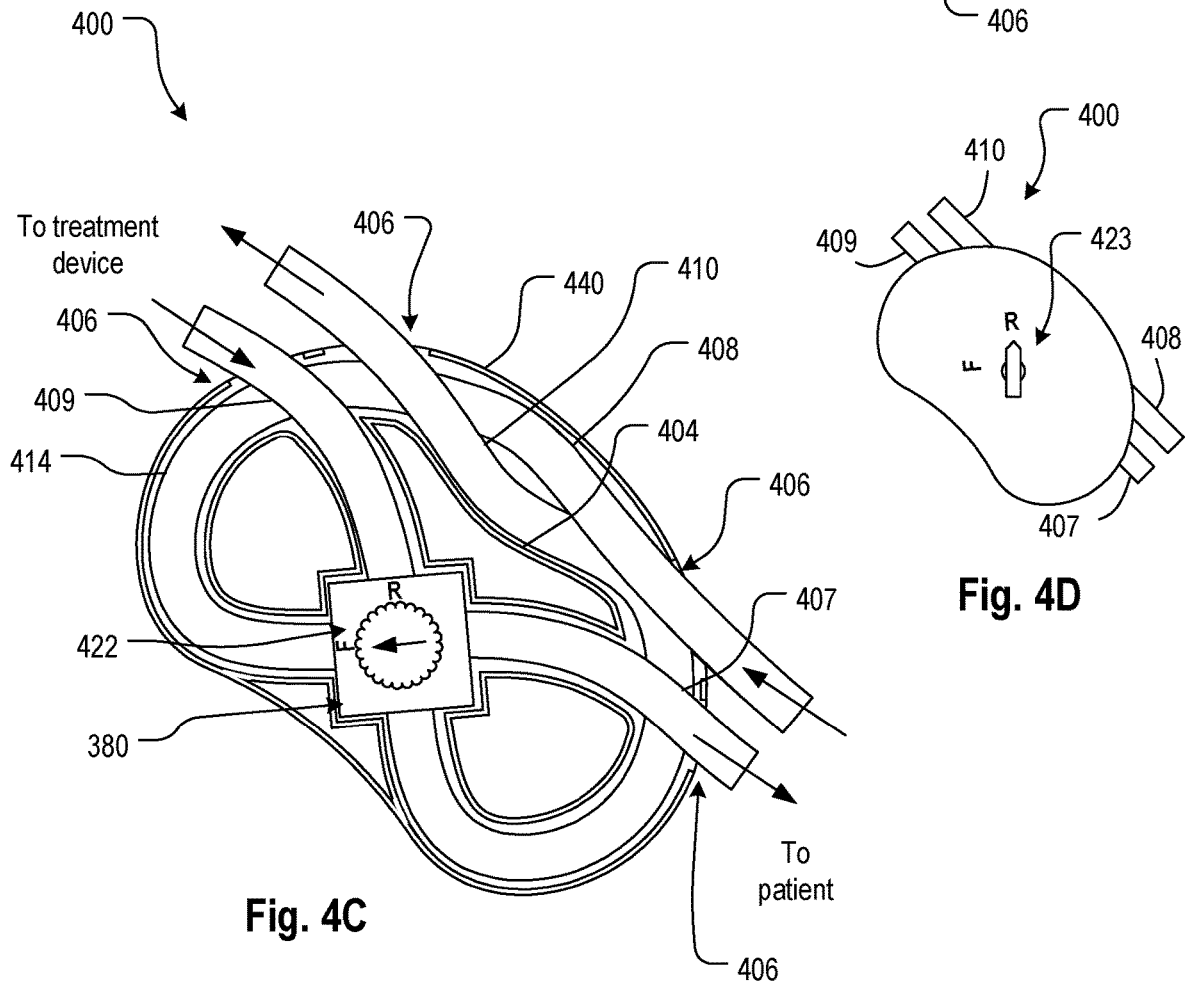
Fig. 4C
Fig. 4D

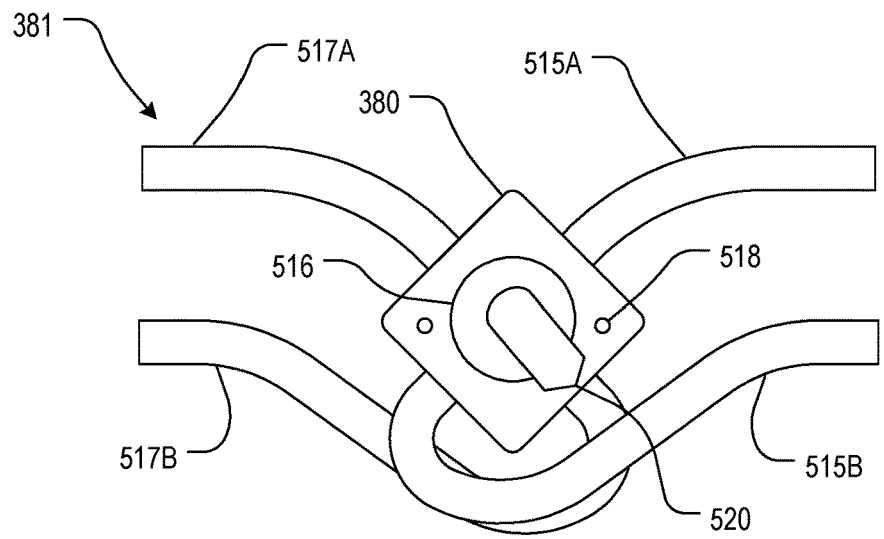
Fig. 6A
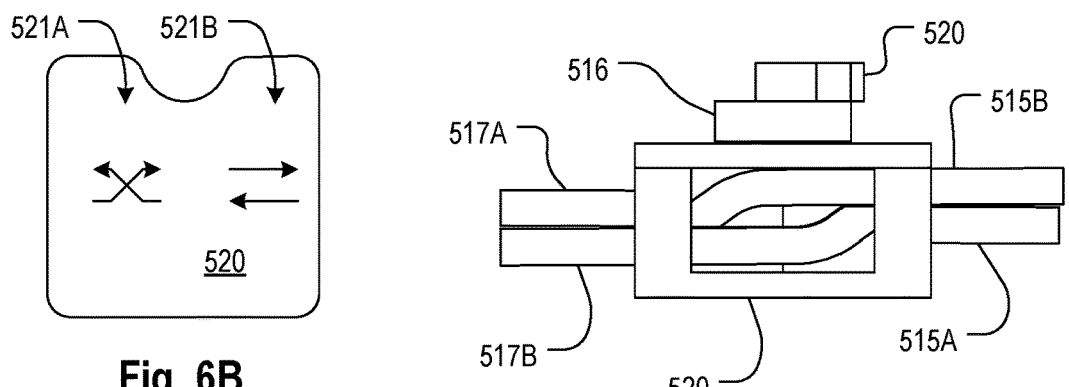
Fig. 6B
Fig. 6C
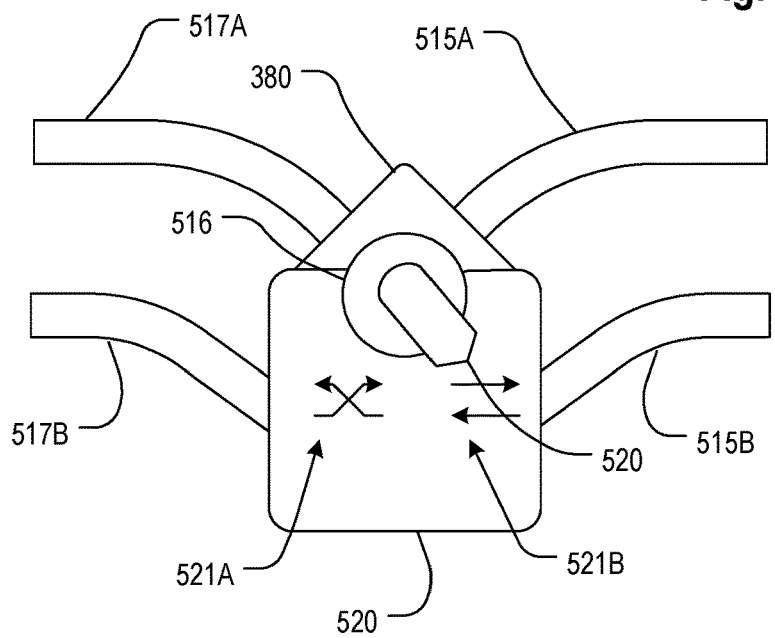
Fig. 6D

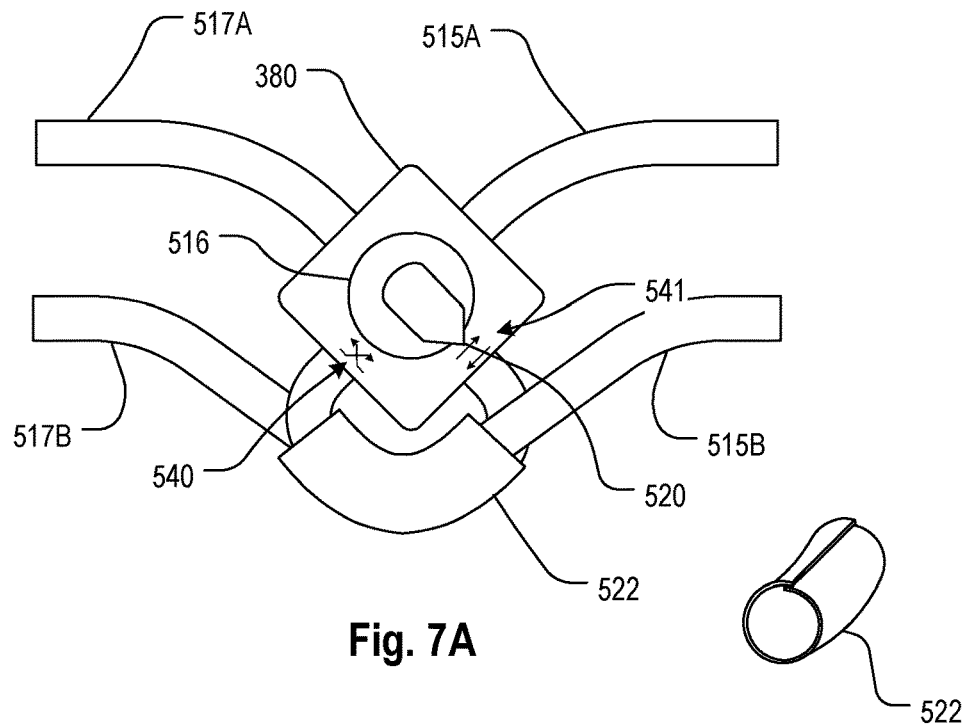
Fig. 7A
Fig. 7B
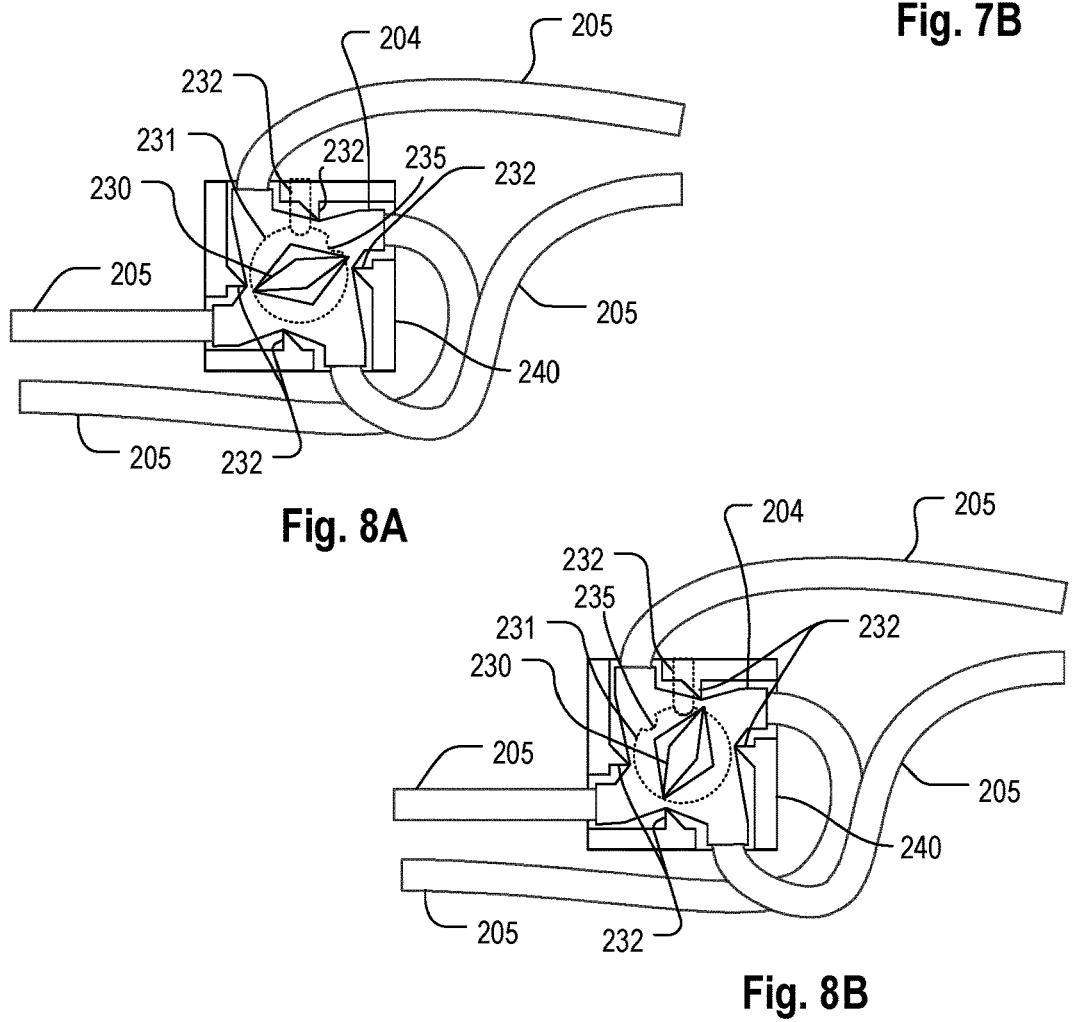
Fig. 8A
Fig. 8B

FLOW REVERSING DEVICE

CROSS REFERENCE TO RELATED APPLICATIONS

This Application is a continuation of U.S. patent application Ser. No. 16/493,563 filed Sep. 12, 2019, which is a U.S. national stage filing under 35 U.S.C. § 371 of International Application No. PCT/US2018/024389, filed Mar. 26, 2018, which claims the benefit of U.S. Provisional Application No. 62/478,518 filed Mar. 29, 2017, each of which are incorporated herein by reference in their entireties.

BACKGROUND

Hemodialysis and other forms of extracorporeal blood treatment require the removal of blood from a patient by means of an arterial set, passing of the blood to a blood processing device such as a dialyzer, and returning of the blood to the patient again through a venous blood set.

Maintenance of a good blood set access is a major cost of dialysis, which is the most common extracorporeal blood treatment, although other types of blood treatment are also used, for example passing of the blood through an absorption bed for removal of toxins and the like, hemoperfusion, and other forms of blood treatment.

Beyond the initial cost of the surgical procedure to establish a fistula or graft in the patient, the keeping of adequate blood flow in an arterialized vein or synthetic arteriovenous graft of the patient frequently involves secondary surgical intervention for reconstruction of an old blood vessel site on the patient. Alternatively, it may be necessary to establish an entirely new fistula or graft at a new site if the old one fails.

Failure is evidenced typically by stenosis of the blood vessel, or blockage of an implanted catheter or other venous access site, with a consequent reduction in blood flow that eventually shuts down the site. Clotting is also a major cause of reduced blood flow.

If site failure is detected early enough, a less invasive technique such as balloon angioplasty can be employed to open the stenosis at a greatly reduced cost. Early detection of stenosis can be measured by change in pressure in the blood vessel or implant that reflects a restriction beginning to form. The technique described in Omachi U.S. Pat. No. 5,454,374 has been used to measure the baseline pressure access site for early detection of such a pressure change. Another method used by clinicians is to measure recirculation in the vessel during dialysis. As the flow is restricted in the access, the blood pumping rate indicated on the dialysis machine may exceed the flow rate of fresh blood coming into the vessel, so that some is recirculated from the venous access site to the arterial access site in the patient. This leads to inadequate dialysis since already cleansed blood is thus being reprocessed.

Various methods for measuring the degree of recirculation of this type are known. Another method described by Krivitsky determines blood flow in the access as a marker for stenosis. In this method blood set flow and recirculation are compared between arterial and venous flow in the normal orientation, and then with reversed flow between the arterial and venous access sites, which are typically fistula needles which enter the vein. In the prior art, clinicians typically accomplish this by stopping the flow of blood, clamping off all the lines, disconnecting the set or sets from the fistula needles, and then reconnecting the arterial line to the venous fistula while connecting the venous line to the arterial fistula.

Also regarding catheters (which are typically connected to larger veins or even the vena cava) it is known that catheter blockage may be relieved by reversing flow.

Catheters which are implanted in the venous system of a patient for dialysis access or the like may develop a "fibrin sheath" on the outside of the catheter within the blood vessel, for example the jugular or subclavian veins or the vena cava. This fibrin sheath coats the outside of the catheter and can extend over the end thereof.

At the outflow port, such a fibrin sheath is generally not too serious a problem since the outflowing blood forces the fibrin sheath open easily. However, at the inflow port of the catheter, the sheath can act as a one-way valve, collapsing with increasing negative pressure to seriously interfere with flow through the catheter.

Upon such an occurrence, a blood flow reversing valve may reverse the flow of blood through the catheter for continuation of a desired medical procedure such as hemodialysis application.

Referring to FIGS. 1A through 1E, a number of alternative designs for four-way valves have been developed for blood circuits. Referring to FIG. 1A, U.S. Pat. No. 5,894,011, discloses a valve that swaps the connections between pairs of lines 905 and 906 via a pair of rotatably connected disks 901 and 902, each of which supports one of the pairs of lines 905 and 906. The latter reference, for purposes of the US designation in the current PCT application, is hereby incorporated by reference in its entirety herein. A seal must be maintained between the disks 901 and 902 and between the respective lines. The device is intended to be operated manually. The parts are required to be rotated 180 degrees and must be rotated to a full lock before the seal and full patency are provided. Also, any indication of the two positions, such as a pointer and label, cannot be placed in a single location so that the position of the valve is indicated by looking at it. For example, if a pointer is positioned on the bottom and rotated 180 degrees from a forward to the reverse position, the pointer cannot be seen from one side as with the configuration of a valve like the quarter-turn type valve of U.S. Pat. No. 4,885,087 discussed below.

Referring to FIG. 1B, another four-way valve, disclosed in U.S. Pat. No. 5,605,630, which has been proposed for use in blood lines, has a rotating wheel 910 with channels 911 and 912 defined between the wheel 910 and the inside of a housing 913. The latter reference, for purposes of the US designation in the current PCT application, is hereby incorporated by reference in its entirety herein. When the wheel is rotated, the channels 911 and 912 shift to join a different pair of lines. This device also has seals.

Referring to FIG. 1C, another arrangement is proposed in U.S. Pat. No. 6,177,049, which for purposes of the US designation in the current PCT application, is hereby incorporated by reference in its entirety herein. This device has a rotating component 915 with channels 921 and 922 defined within it. As the rotating component 915 is rotated, the channels defined between pairs of lines 917 and 919 change from parallel lines joining one set of corresponding lines to U-shaped channels joining a different set.

Referring to FIGS. 1D and 1E, a design, disclosed in U.S. Pat. No. 4,885,087, for purposes of the US designation in the current PCT application, hereby incorporated by reference in its entirety herein, is very similar to that of FIG. 1B. This design has a rotator 925 that connects different pairs of lines depending on the position thereby defining two different sets of possible flow channels 926 and 929 or 927 and 931.

Referring to FIG. 1E, another type of four-way valve is formed by interconnecting two tubes 937 and 938 with crossover lines 935 and 936. This design is disclosed in U.S. Pat. No. 6,189,388 (Hereafter, "U.S. Pat. No. '388"), which for purposes of the US designation in the current PCT application, is hereby incorporated by reference in its entirety herein. Tube pinching actuators 941-944 are used to force fluid through different channels, depending on which actuators are closed. This device provides a hermetic seal and can be fairly inexpensive, but in a given configuration, significant no-flow areas are defined. These dead spaces can lead to the coagulation of blood, which is undesirable. Also, the interconnection of tubes in this does not lend itself to automated manufacturing.

Another type of four-way valve is based on the generally configuration of FIGS. 1H through 1L except that it is motor-actuated. A pinching mechanism achieves selection of opposite loop branches to switch flow paths by rotating a cam in the middle of the loop. The displacement of the cam can be less than 90 degrees between the two stop positions. This configuration is described in U.S. Pat. No. 8,002,727, which for purposes of the US designation in the current PCT application, is hereby incorporated by reference in its entirety herein.

Solutions known in the prior art include U.S. Pat. No. 6,177,049, for "Reversing Flow Blood Processing System," which discloses a blood processing system having a reverse flow valve therein so that flow through the arterial and venous fistulas, or other equivalent patient connection equipment, can be reversed without reversing or stopping the blood pump. Another solution known in the prior art is U.S. Pat. No. 6,319,465 for "Reversing flow blood processing system having reduced clotting potential." Referring to FIG. 1G, another type of flow reversing valve of simple construction is shown by U.S. Pat. No. 4,885,087 for "Apparatus for mass transfer involving biological/pharmaceutical media." The valve described by the latter disclosure is of simple construction and is very intuitive and easy for a user to change the flow direction by rotating a lever. The general design of a lever and a cross-shaped set of tubes follows a manual reversing valve design used in plumbing systems as shown in the figure below.

Another very simple and inexpensive design uses a loop 204 from which four tubes 205 stem. The loop 204 can be made up of 4 T-shaped junctions fitted together so that the four tubes 205 extending radially from it. A double tube-pinching clamp 202, is shown in side and top views at 202A and 202B respectively. The double tube-pinching clamp 202 is positioned as shown in FIG. 1K to reverse (as shown in FIG. 1L) the flow between pairs of tubes. Although this configuration has a low cost of manufacture, some users may find it difficult to understand completely creating a training burden and concomitant risk. It will be observed that the routing of the tubes to make side-by-side sets of counter-current flows is not apparent from the way the tubes stem from the loop 204.

One feature of many of the prior art configuration is that they have tubes coming out of the flow switch that cross, when a first pair of tubes is extended toward the patient and a second pair of tubes is extended toward the treatment device. This can form a confusing arrangement. Although U.S. Pat. No. 6,319,465 does not have this drawback—the blood tubes extending to the patient extend from the same side and the blood tubes extending to the treatment device extend from an opposite side— the configuration is complex and expensive to manufacture and can be unintuitive to use.

SUMMARY

The drawbacks of the prior art are overcome by providing a flat rotary switch type of valve as described in U.S. Pat. No. 4,885,087 without the drawbacks identified above and with additional benefits as herein described. First, the problem of crossing blood lines is resolved by providing an external support that routes the tubing in such a manner that the patient connection tubes extend from one end of the device and the treatment device tubes extend from the opposite end. The external support may provide guides that hold the tubing extending from the supported flat rotary switch type of valve so as to keep them from being pinch or kinked thereby ensuring free flow of blood. The flow switch is supported by the external support which can also support indicia indicating the switch position. The external support can include an enclosure. The enclosure may be of an ergonomic design that fits comfortably in the hand. In embodiments, the ergonomic design is asymmetrical to provide an indication or orientation.

Objects and advantages of embodiments of the disclosed subject matter will become apparent from the following description when considered in conjunction with the accompanying drawings.

BRIEF DESCRIPTION OF DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 4A through 4D show a reversing valve device according to embodiments of the disclosed subject matter.

FIGS. 6A through 6D show an embodiment of a support for routing tubes to achieve many of the technical functions described with regard to other embodiments in a compact form and without a full enclosure, according to embodiments of the disclosed subject matter.

FIGS. 7A and 7B shows an embodiment of a support that provides routing of tubes from opposite sides of the four-way valve without enclosing or even being directly connected to the four-way valve, according to embodiments of the disclosed subject matter.

FIGS. 8A and 8B show a cam-type actuator actuating a loop type flow reversal device as shown in the embodiment of FIGS. 1H and 1J through 1L which allows a four way valve to be formed without any seals, may provide an angular displacement of less than 90 degrees, and which employs a détente mechanism to lock the rotating cam, according to embodiments of the disclosed subject matter.

DETAILED DESCRIPTION

Figure 2:
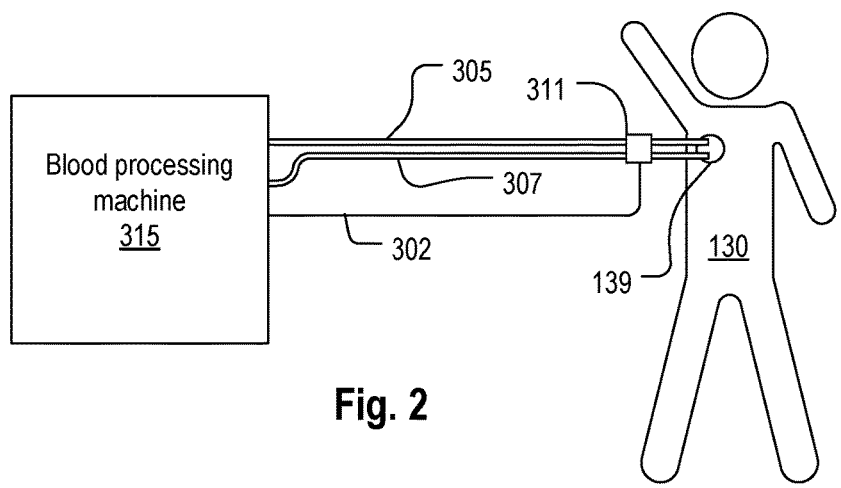
FIG. 2 illustrates a flow circuit including a blood treatment machine and a reversing valve, according to embodiments of the disclosed subject matter.

Referring now to FIG. 2, a patient 130 is connected by an access 139 to a blood processing machine 315. The latter draws blood through an arterial blood line 305 and returns treated blood to the patient 130 through a venous blood line 307. The blood processing machine 315 may be any treatment device such as a hemodialysis machine, a hemofiltration machine, an infusion pump (in which case no arterial line 305 would be present), etc.

Access 139 may consist of various devices such as a fistula (not shown) and catheter (not shown) combination or other type of access which may be disconnected by various means. For example, a catheter (not shown) may be withdrawn from a fistula (not shown) and/or the catheter (not shown) disconnected from the arterial 307 and venous 305 lines by means of a luer connector (not shown). The above are conventional features of which a variety of alternatives are known.

A reversing valve 311 causes the arterial line at the patient end to switch places selectively with the venous line and the patient end. This causes the blood to flow in an opposite direction at the patient end; through the patient access.

Figure 3A:
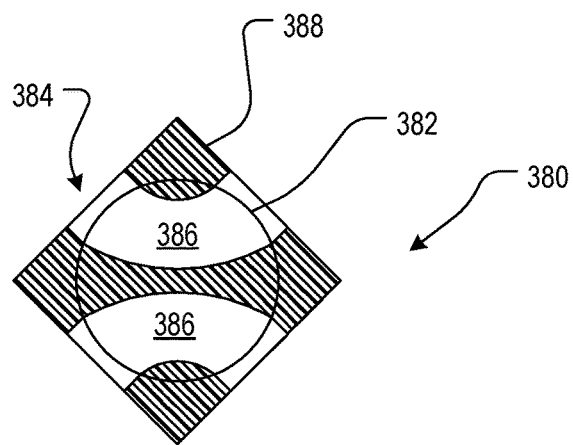
FIGS. 3A through 3E show a reversing valve and various features thereof, according to embodiments of the disclosed subject matter.
Figure 3D:
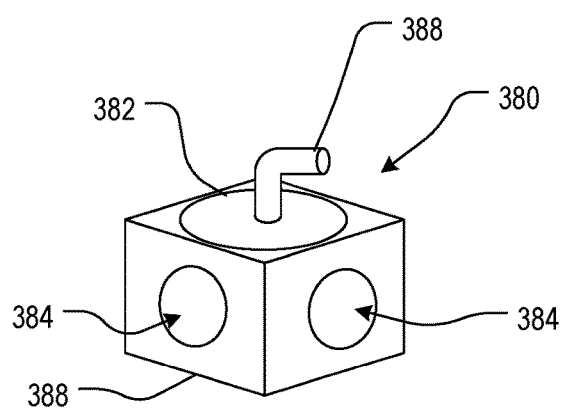
Figure 3B:
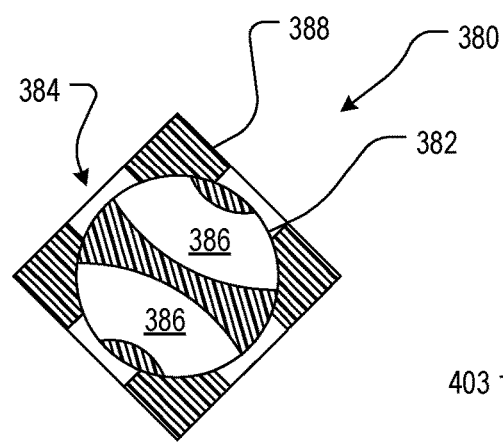
Figure 3C:
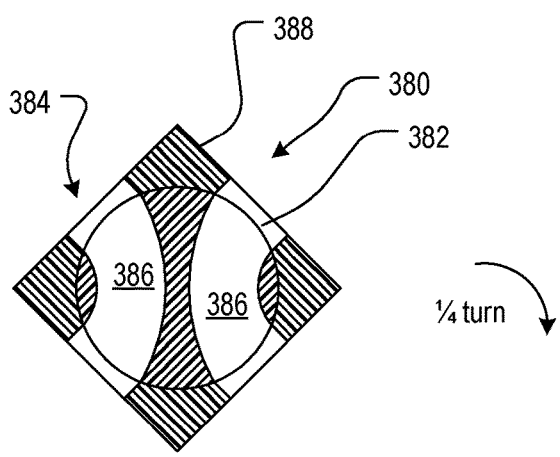

Referring to FIGS. 3A, 3B, and 3C, a reversing valve 380 (also called a 4-way valve) is shown in section. The reversing valve 380 has a rotating element 382 with channels 386 within a port block 388. The rotating element 382 forms a seal with the port block 388. The port block provides ports 384 for attachment of tubes. Tubes may be bonded by welding or by adhesive. The valve operates according to the same principles as prior art embodiments disclosed above. FIGS. 3A, 3B, and 3C show the rotating element 382 in a first position, an intermediate transition position, and a second position respectively. The first and second positions provide parallel and reverse flow respectively. FIG. 3D shows a perspective view of the reversing valve 380. The details of the embodiment of FIGS. 3A through 3D are a mere example of a configuration suitable for manufacturing of biocompatible materials. Other shapes of the elements are known in the prior art and may readily be devised based on the basic principles herein disclosed. As will be more evident after the discussion of the embodiments of FIGS. 4A through 4D, the features of the reversing valve 380 that are particularly relevant to the disclosed subject matter include the following.

Figure 1A:
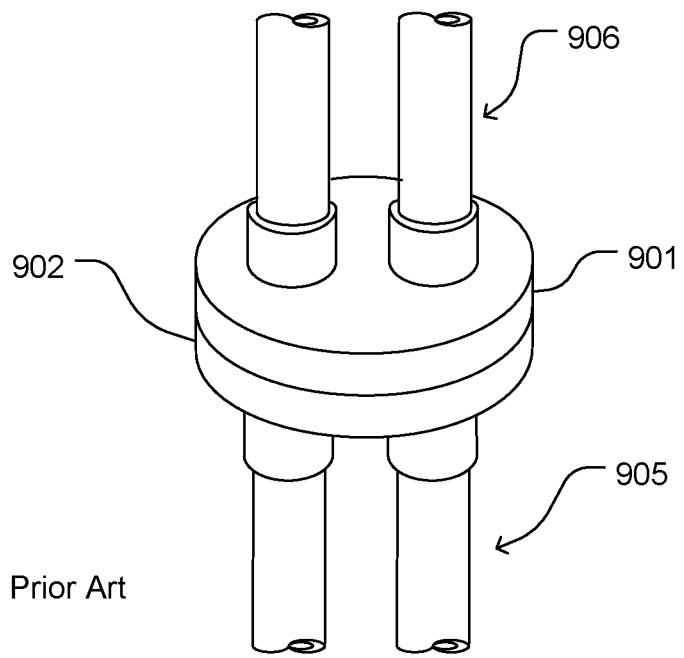
FIGS. 1A-1H and 1J-1L illustrate various flow reversing devices according to the prior art.
Figure 1B:
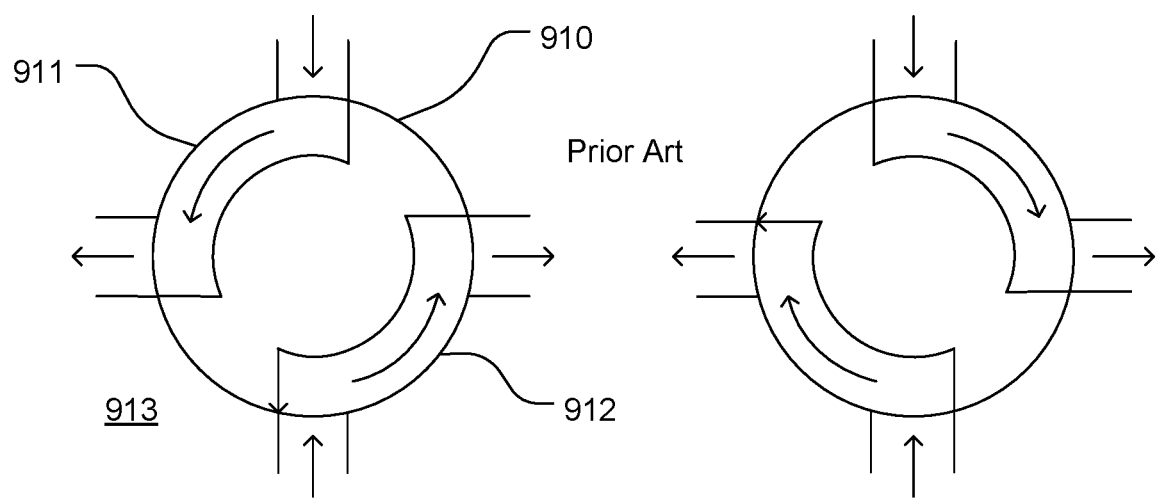
Figure 1C:
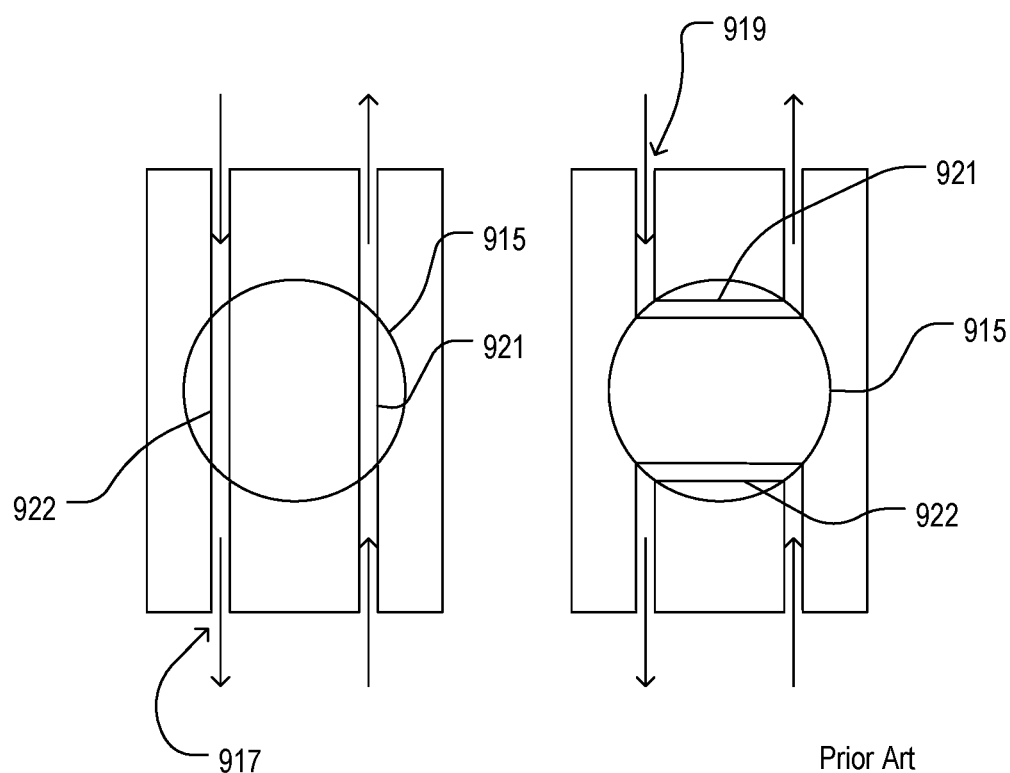
Figures 1D, 1E:
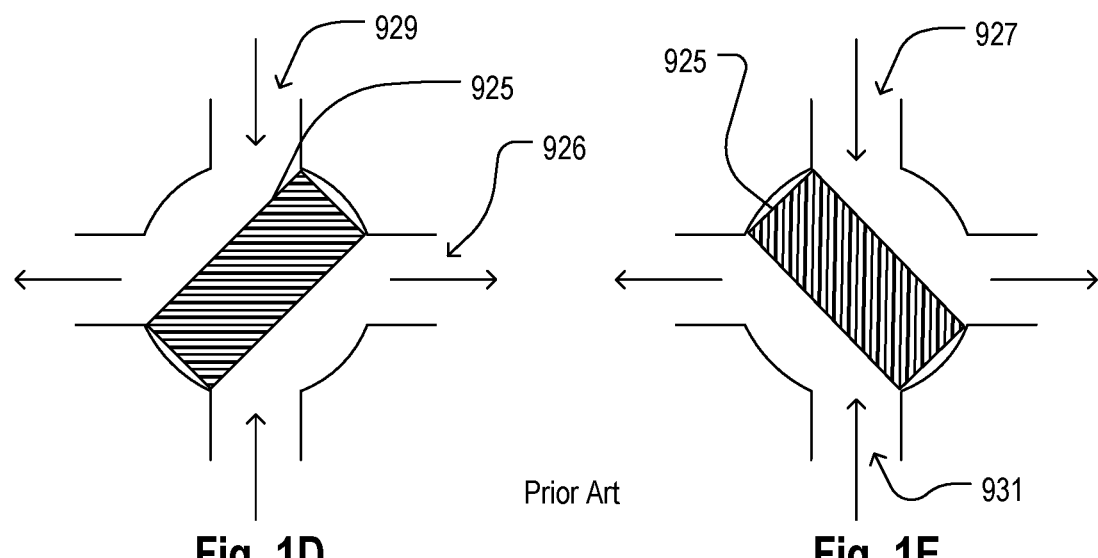
Figure 1F:
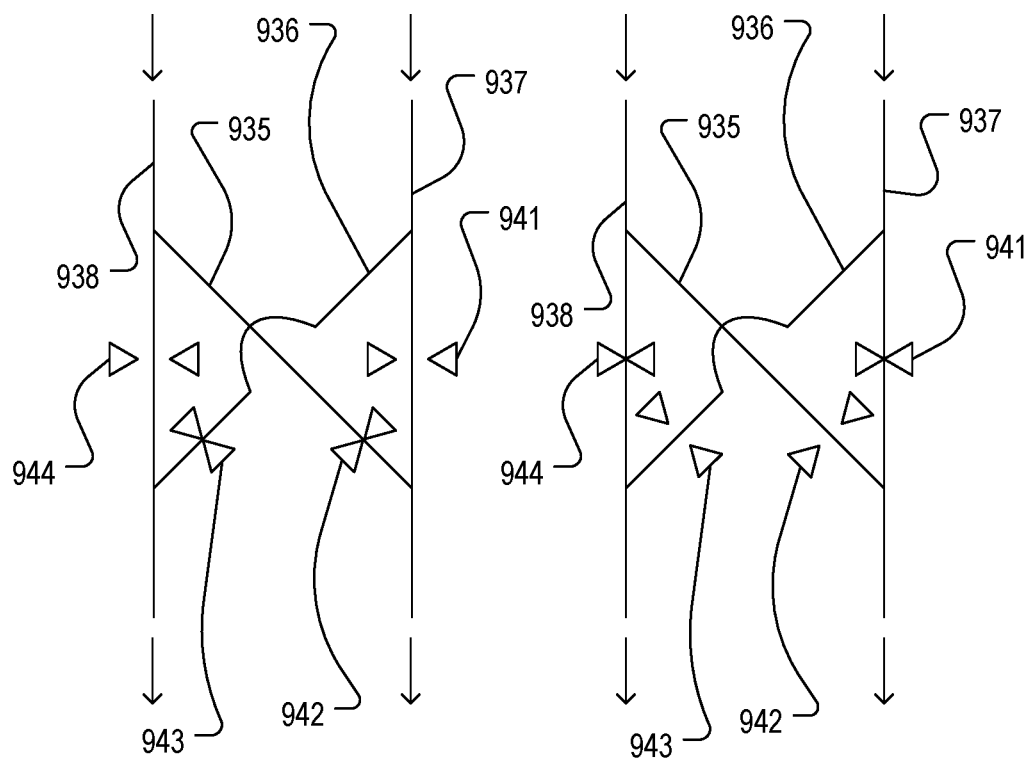
Figure 1G:
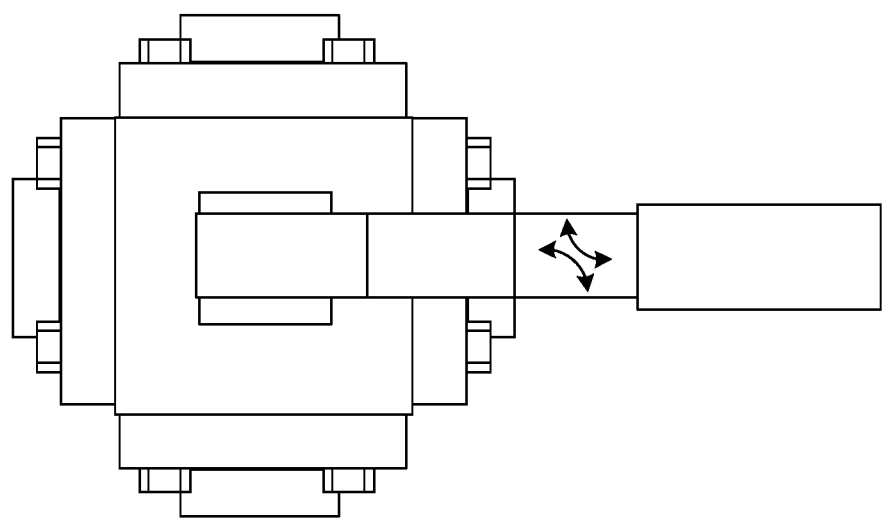
Figure 1H:
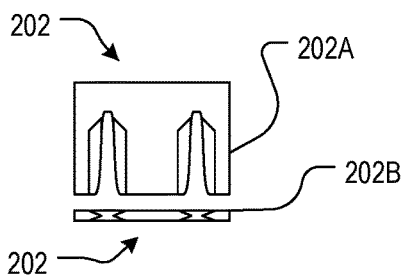
Figure 1J:
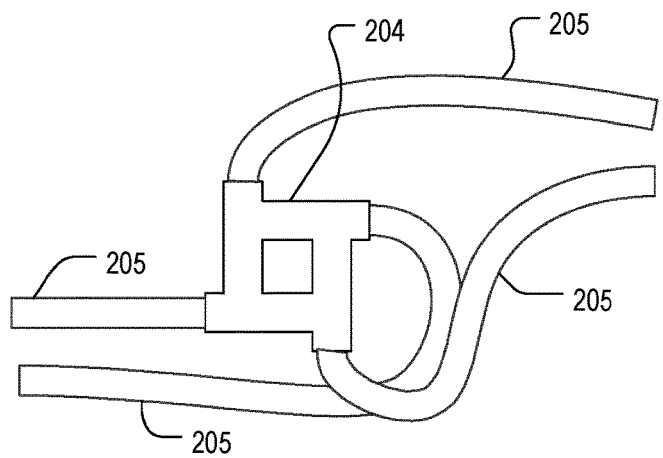
Figure 1K:
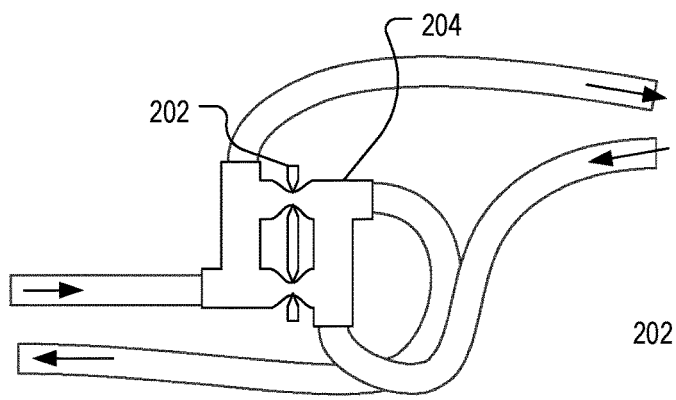
Figure 1L:
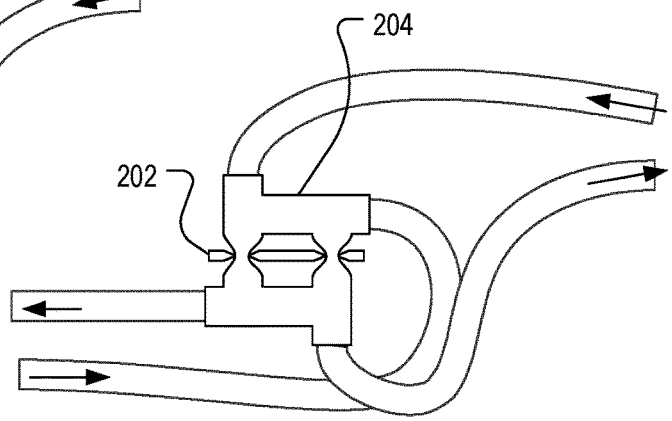

1. The angular displacement from a side of the reversing valve 380. That is the axis of rotation is provided on a flexible face of the reversing valve 380, unlike the prior art configuration FIG. 1A where tubes are aligned with the axis of rotation. That is, the tubes stem from the valve parallel to the axis and therefor do not allow the attachment of an actuation element such as a handle 388 to switch the valve.

2. The magnitude of rotation required to switch the valve is less than 180 degrees and preferably about 90 degrees. This makes it more convenient to switch.

Figure 3E:
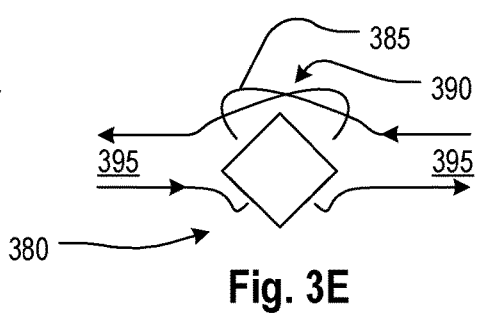

3. As illustrated in FIG. 3E, the configuration is such that for use in configuration where the valve is to be applied in an application that establishes counter-current parallel flow paths indicated at 395 that extend away from the valve in opposite directions, the tubing 385 connected to the valve 380 must cross 390 as shown in FIG. 3E.

Figure 4A:
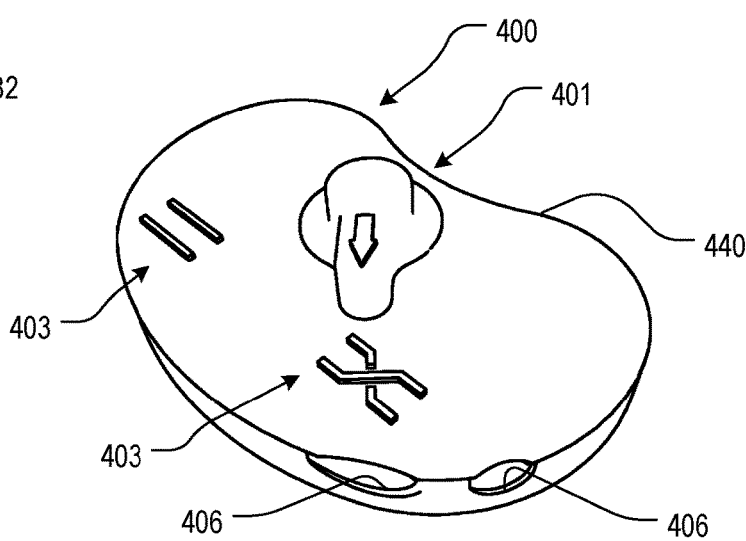

Referring now to FIG. 4A a reversing valve device 400 has a housing 440 with a flow switch handle 401. The flow switch handle is connected to a reversing valve within the housing that has the 3 features enumerated above. The enclosure 440 has openings 406 that permit tubes to extend away from the reversing valve device 400 in pairs in opposite directions or on opposite sides of the reversing valve device 400. Referring to FIGS. 4B and 4C, which show the inside of the reversing valve device 400. To provide the configuration where respective pairs of inflow and outflow tubes extend from opposite sides of the house, the housing 440 is provided with guides that guide tubes in a fashion that holds the crossing tubes in the housing. In this way the device can provide a clean appearance and an easy-to-hold shape as shown in FIG. 4D.

A first pair of counter-current tubes 409 and 410 are connected on opposites side of the reversing valve 380. A second, different, pair of counter-current tubes 407 and 408 are also connected on different opposites side of the reversing valve 380. The tubes 408 and 410 are held in a crossing arrangement. In the present embodiment, the tubes are supported in channels that help to ensure there are no kinks in the tubes despite the tortuous path followed by tubes 408 and 410. The arrangement can be open of fully enclosed by a housing. Other types of supports can provide a similar effect. It will be evident that the enclosure can be formed from two separate halves each of which can be molded in a simple single-shot two-part mold. It will also be evident that the enclosure 440 can have a variety of shapes. Various different handles for activating the valve may be provided. The drawings show a round knurled knob 422 and a blade-shaped handle 423 as examples. FIG. 4D shows another view similar to the view of FIG. 4A.

Figure 5A:
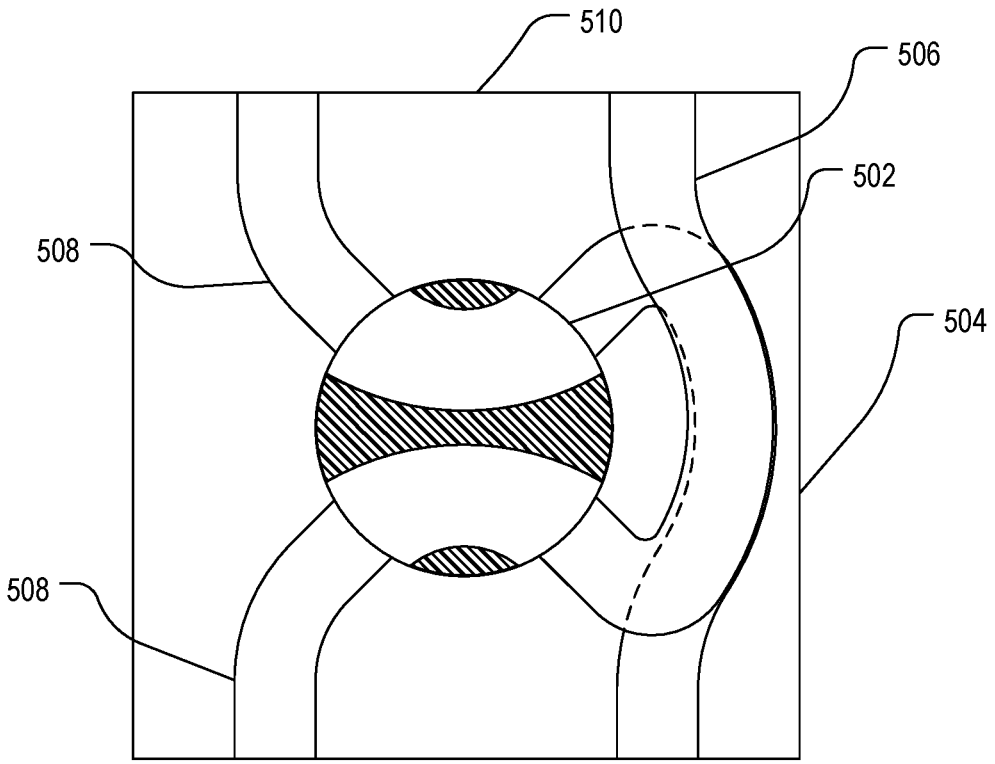
FIGS. 5A and 5B show a 3D printable version of a reversing valve with smooth channels embedded in a valve body to provide mutually adjacent pairs of counter current ports on the valve body, according to embodiments of the disclosed subject matter.
Figure 5B:
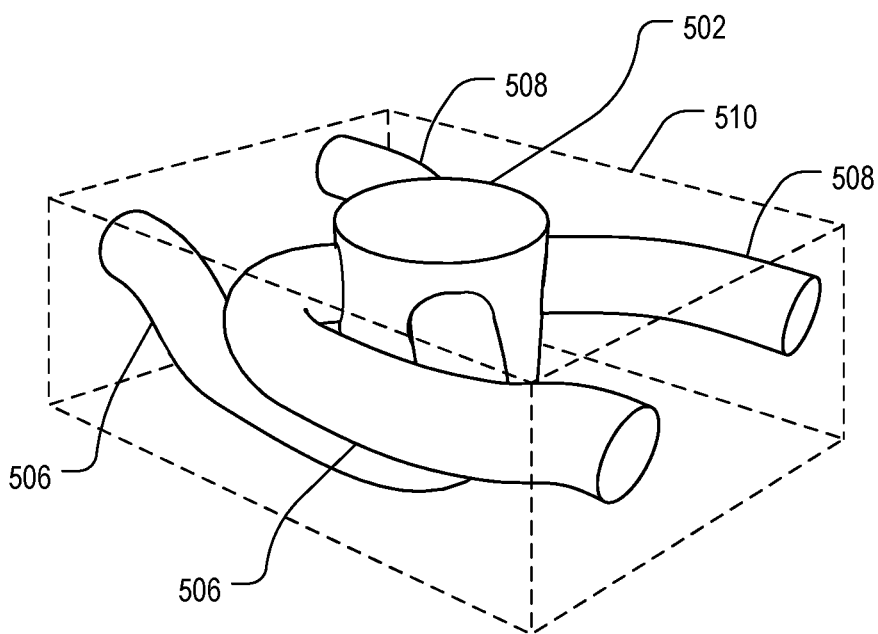

FIGS. 5A and 5B shows a 3D printable version of a reversing valve with smooth channels embedded in a valve body to provide mutually adjacent pairs of counter current ports on the valve body. A valve body 510 may be 3D printed to define channels 506 that cross and channels 508 that do not cross. The valve body 510 may be formed to seal with a stopcock 502 that provides the reversing valve function. It will be evident by inspection that the reversing valve function is provided and that mutually adjacent pairs of counter current ports on the valve body can provide counter current flow from and to a remote device. The features of this device are as described in connection with the foregoing embodiments except separate tubes and a separate enclosure are not required.

FIGS. 6A through 6D show an embodiment of a support for routing tubes to achieve many of the technical functions described with regard to other embodiments in a compact form and without a full enclosure, according to embodiments of the disclosed subject matter. FIG. 6A shows a four-way valve device 381 which may have many specific details, but in this instance is depicted as one similar in configuration and functionally the same as the embodiment of FIGS. 3A through 3E. In the present embodiment, the four-way valve has an actuator 516 with a pointer 520. Tubes 515A, 515B, 517A, 517B stem from a reversing valve 380 in radial directions and such a first pair 515A and 515B that attach to one device are located opposite each other and second pair 517A and 517B that attach to another device are located opposite each other, assuming the flow switch is used for changing a flow direction between two devices such as a source and return of fluid being one device and a consumer—receiver and return—being another. Here again, to allow the pairs to be arranged to help make it evident which tubes attach to each device, tubes 515B and 517B are crossed. A support 520 partially encloses the crossing tubes 515B and 517B and attaches to the four-way valve 380 by capturing it with pins (not shown) that fit into locator holes 518 in the four-way valve 380. Indicia 521A and 521B, similar to those described above with reference to FIG. 4A, may be provided on the support 520. The final configuration is shown in FIG. 6D. It will be evident from inspection that the tubes are held in a configuration in which pairs are formed between tubes are arranged in pairs with one pair 515A and 515B arranged so that it is evident that it attaches to one device located opposite the second pair 517A and 517B that attach to another device. The arrangement makes the attachments apparent by pairing the tubes that connect to one device, that is, placing them close to each other than the tubes that connect to the other device. The arrangement also makes the attachments apparent by placing the tubes that connect to one device opposite those that connect to the other device. These features, it will be observed, are as in other embodiments described herein.

FIGS. 7A and 7B show an embodiment of a support that provides routing of tubes from opposite sides of the four-way valve without enclosing or even being directly connected to the four-way valve, according to embodiments of the disclosed subject matter. The arrangement is the same as the flow-switch 381 of FIG. 6A except that the actuator has indicia 540 and 541 directly on it and there are no locator holes 518. A sleeve 522 is positioned over the crossing tubes 515B and 517B. The sleeve 522 may be a flexible of any suitable construction for example a metal spring, a textile piece with a Velcro closure, or a springy element (plastic, metal) that snaps over the tubes and holds them to a shape conforming to its shape such the curved shape shown. Other arrangements such as even wire ties will be readily apparent from the disclosure.

FIGS. 8A and 8B show a cam-type actuator actuating a loop type flow reversal device as shown in the embodiment of FIGS. 1H and 1J through 1L which allows a four-way valve to be formed without any seals, may provide an angular displacement of less than 90 degrees, and which employs a détente mechanism to lock the rotating cam, according to embodiments of the disclosed subject matter. A support 240 has bosses 232 arrayed around a perimeter thereof and projecting inwardly to pinch a tubing loop 204 as described with reference to FIGS. 1H and 1J through 1L. The fame 240 has a pivoting cam element 230 that rotates to pinch an opposing pair of legs of the loop 204 in each position. FIG. 8A shows the cam element 230 in one position whereby a flow may be established in a forward direction and FIG. 8B shows the cam element 230 in a second position whereby a flow may be established in a reverse direction. Note that throughout the disclosure the distinction between forward and reverse may exist at a system level so the designations may be arbitrary for purposes of the present disclosure of the flow switching device apart from a connected system. A détente mechanism including a pin 232 urged toward a cam 231 maintains the position of the cam element 230 on each of the forward and reverse positions. The pin may be urged by a spring or other device suitable for causing the device to operate as a détente mechanism. A handle may be provided for actuating the cam element 230 manually. A handle is not shown but the form and means for affixing one to the cam element should be evident from general knowledge and the disclosure. It will be apparent by inspection that the range of motion of the cam element 230 between the forward and reverse détente positions is less than 90 degrees. Also, it should be apparent that the loop 204 should be formed of a flexible material to permit it to be deformed as illustrated. Further, the cm element 230 may have a slippery surface so that it does not overly distort the loop 204 when it moves. For example the cam element 230 may have a fluorocarbon coating or it may have small rollers.

Figure 9A:
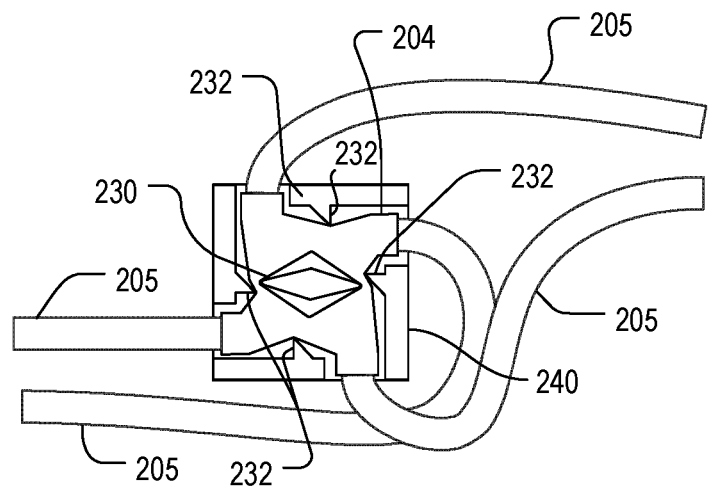
FIGS. 9A and 9B show a cam-type actuator actuating a loop type flow reversal device as shown in the embodiment of FIGS. 1H and 1J through 1L which allows a four way valve to be formed without any seals, may provide an angular displacement of less than 90 degrees, and which permits over-rotation of the internal cam and the resilience of the outside cams to provide the function of a détente mechanism without an additional component, according to embodiments of the disclosed subject matter.
Figure 9B:
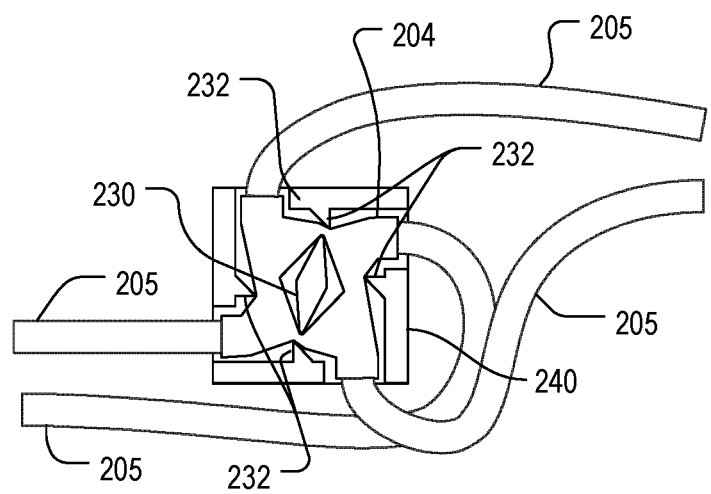

FIGS. 9A and 9B show a cam-type actuator actuating a loop type flow reversal device as shown in the embodiment of FIGS. 1H and 1J through 1L which allows a four way valve to be formed without any seals, may provide an angular displacement of less than 90 degrees, and which permits over-rotation of the internal cam and the resilience of the outside bosses to provide the function of a détente mechanism without an additional component, according to embodiments of the disclosed subject matter. Instead of providing a separate détente mechanism, stops (not shown) permit the cam element 230 to rotate past the positions of a respective the bosses 232 to compress the walls of the tubing of which the legs are formed and/or resiliently bend the bosses 232 thereby locking the tips of the cam element 230 behind the bosses 232 and locking the cam element in a corresponding forward or reverse position.

According to embodiments, the disclosed subject matter includes a flow reversing device. A flow reversing valve is of a type that switches by angular displacement of an actuator element thereof that is accessible from a side thereof, there being no ports or tubes extending from said side. The flow reversing valve provides full reversal with less than 180 degrees of rotation. Two pairs of tubes extend from respective opposite sides of the flow reversing valve. A support holds the flow reversing valve and tubes extending away therefrom such that each pair of tubes emerges from the support on opposites sides of the support.

In variation, the support encloses the flow reversing valve and crossing portions of two of the tubes. In further variations, the support encloses the flow reversing valve and crossing portions of two of the tubes, the two of the tubes belonging to different ones of said pairs.

In still further variations, the support encloses the flow reversing valve and crossing portions of two of the tubes forming an enclosure, the enclosure being kidney-shaped.

In yet more variation, the flow reversing valve has an actuator handle that is asymmetric and functions as a pointer to indicia on the support indicating forward and reversed positions of the flow reversing valve.

According to further embodiments, the disclosed subject matter includes a flow reversing device. A flow reversing valve is of a type that switches by angular displacement of an actuator element thereof that is accessible from a side thereof, there being no ports or tubes extending from said side. The flow reversing valve provides full reversal with less than 180 degrees of rotation. In embodiments, the reversal happens with about 90 degrees of rotation. Two pairs of tubes extend from respective opposite sides of the flow reversing valve. A support holds the flow reversing valve and tubes such that they extend away therefrom and such that each pair of tubes emerges from the support mutually adjacent positions.

In variations of the further embodiments, the support encloses the flow reversing valve and crossing portions of two of the tubes. In further variations of the further embodiments, the support encloses the flow reversing valve and crossing portions of two of the tubes, the two of the tubes belonging to different ones of said pairs. In variations of the further embodiments, the support encloses the flow reversing valve and crossing portions of two of the tubes forming an enclosure, the enclosure being kidney-shaped. In variations of the further embodiments, the flow reversing valve has an actuator handle that is asymmetric and functions as a pointer to indicia on the support indicating forward and reversed positions of the flow reversing valve.

According to still more embodiments, the disclosed subject matter includes a flow reversing device with a flow reversing valve of a type that switches by angular displacement of an actuator element thereof that is accessible from a side thereof, there being no ports or tubes extending from the side. The flow reversing valve provides full reversal with less than 180 degrees of rotation. There are two pairs of tubes, the members of each pair originating and extending from respective opposite sides of the flow reversing valve. A support holds the flow reversing valve and tubes extending away therefrom such that each pair of tubes emerges from the support on opposites sides of the support. In variations of any embodiment, the support encloses the flow reversing valve and crossing portions of two of the tubes. In variations of any embodiment, the support encloses the flow reversing valve and crossing portions of two of the tubes, the two of the tubes belonging to different ones of the pairs. In variations of any embodiment the support encloses the flow reversing valve and crossing portions of two of the tubes forming an enclosure. In variations of any embodiment the support holds two of the tubes such that they cross each other with each of the two forming one of each of the two pairs. In variations of any embodiment the support has indicia indicates forward and reverse flow directions and the flow reversing valve has an actuator handle that is asymmetric and functions as a pointer to indicia on the support indicates forward and reversed positions of the flow reversing valve. In variations of any embodiment the support has indicia indicates forward and reverse flow directions and the flow reversing valve has an actuator handle that is asymmetric and functions as a pointer to indicia on the support indicates forward and reversed positions of the flow reversing valve, the support, defining an enclosure, having multiple external major faces and the indicia being on a same one of the external faces. In variations of any embodiment the flow reversing valve provides full reversal with no more than 90 degrees of rotation.

According to still more embodiments, the disclosed subject matter includes a flow reversing device. In the device, a flow reversing valve is of a type that switches by angular displacement of an actuator element thereof that is accessible from a side thereof, there being no ports or tubes extending from the side. The flow reversing valve provides full reversal with less than 180 degrees of rotation. There are two pairs of tubes, the members of each pair extending from respective opposite sides of the flow reversing valve. A support holds the flow reversing valve and tubes extending away therefrom such that each pair of tubes emerges from the support adjacent each other.

In variations of any embodiment the support encloses the flow reversing valve and crossing portions of two of the tubes. In variations of any embodiment the support encloses the flow reversing valve and crossing portions of two of the tubes, the two of the tubes belonging to different ones of the pairs. In variations of any embodiment the support encloses the flow reversing valve and crossing portions of two of the tubes forming an enclosure. In variations of any embodiment the support holds two of the tubes such that they cross each other with each of the two forming one of each of the two pairs. In variations of any embodiment the support has indicia indicates forward and reverse flow directions and the flow reversing valve has an actuator handle that is asymmetric and functions as a pointer to indicia on the support indicates forward and reversed positions of the flow reversing valve. In variations of any embodiment the support has indicia indicates forward and reverse flow directions and the flow reversing valve has an actuator handle that is asymmetric and functions as a pointer to indicia on the support indicates forward and reversed positions of the flow reversing valve, the support, defining an enclosure, having multiple external major faces and the indicia being on a same one of the external faces. In variations of any embodiment the flow reversing valve provides full reversal with no more than 90 degrees of rotation.

According to still further embodiments, the disclosed subject matter includes a flow reversing device in which a valve body has four ports and a rotating stopcock having multiple channels therein. The four ports and the multiple channels are arranged to provide a flow reversing valve function when the stopcock is rotated by an angular displacement of less than 180 degrees. An actuator element on a side of the stopcock is accessible from a side of the valve body, there being no ports facing the side. The four ports form first ends of channels within the valve body with second ends opening to an external face of the valve body. There are two pairs of the second ends, each pair being mutually adjacent on the external face with each pair connecting to respective members of the other pair in both positions of the rotating stopcock. In variations of any embodiment the two of the channels cross are spaced apart along an axis of rotation of the stopcock to permit them to cross each other to opposite sides of the valve body. In variations of any embodiment the stopcock has an actuator handle that is asymmetric and functions as a pointer to indicia on the valve body. In variations of any embodiment the valve body is 3D-printed.

According to yet more embodiments, the disclosed subject matter includes a flow reversing device with a flow reversing valve of a type that switches by angular displacement of an actuator element thereof that is accessible from a side thereof, there being no ports or tubes extending from the side. The flow reversing valve provides full reversal with less than 180 degrees of rotation. There are two pairs of tubes, the members of each pair originating and extending from respective opposite sides of the flow reversing valve. In variations of any embodiment a support holds the flow reversing valve and tubes extending away therefrom such that the tubes of each pair are mutually adjacent. In variations of any embodiment the support holds the pairs of tubes such that they are located on opposites sides of the support. In variations of any embodiment the support holds the tubes such that one of each pair is parallel or collinear with one of the other pair. In variations of any embodiment the support encloses the flow reversing valve and crossing portions of two of the tubes. In variations of any embodiment the support encloses the flow reversing valve and crossing portions of two of the tubes, the two of the tubes belonging to different ones of the pairs. In variations of any embodiment the support encloses the flow reversing valve and crossing portions of two of the tubes forming an enclosure, the enclosure being kidney-shaped. In variations of any embodiment the flow reversing valve has an actuator handle that is asymmetric and functions as a pointer to indicia on the support indicates forward and reversed positions of the flow reversing valve.

According to yet embodiment, the disclosed subject matter includes method of routing four tubes from a four-way valve in which tubes extend from a flow switch in four directions, two of which directions are orthogonal to the other two directions. The method includes routing a first of the four tubes to position it adjacent to a second of the four tubes stemming from a side of the flow switch opposite a side of the flow switch from which the first of the four tubes stems. The method further includes routing a third of the four tubes to position it adjacent to a fourth of the four tubes stemming from a side of the flow switch opposite a side of the flow switch from which the third of the four tubes stems. The method further includes fixing the four tubes in a position resulting from the first and second routings. In variations of any embodiment the fixing includes at least partially enclosing the flow switch. In variations of any embodiment the method includes providing access to an actuator of the flow switch by means of a handle residing at least partially outside an enclosure resulting from the at least partially enclosing.

In variations, the methods may include indicating a position of the flow switch actuator by aiming a pointer of the handle at a respective indicium on the enclosure. The first and second routings may cause the first and third tubes to cross each other. Each of the four tubes may stem from the flow switch initially at 90 degrees from two nearest neighboring ones of the four tubes. In variations of any embodiment the two of the four tubes a curved such that each stems from an enclosure resulting from the enclosing at 45 degrees from an angle at which it stems from the flow switch. In variations of any embodiment the two of the four tubes a curved such that each stems from an enclosure resulting from the enclosing at 135 degrees from an angle at which it stems from the flow switch. In variations of any embodiment the flow switch has two stop positions corresponding to forward and reverse flow configurations and the pointer of the handle points to the first and second tubes when the handle is positioned in one stop position and to the third and fourth tubes when handle is positioned in the other stop position. In variations of any embodiment the flow switch has two stop positions corresponding to forward and reverse flow configurations and the two stop positions are affected by an angular displacement of the handle that is no more than 90 degrees.

According to still further embodiments, the disclosed subject matter includes a flow switch device with a loop of tubing with four tubing branches extending from it, the loop having two pairs of opposed tubing legs. A support has four sides each having a boss that engages with a respective one of the tubing legs making up the two pairs. A cam element is inside the loop. In a first rotational position, the cam element pinches one of the two pairs of opposed tubing legs and in a second rotational position pinches another of the two pairs of opposed tubing legs. A détente mechanism releasably holds the cam element in each of the first and second rotational positions when the cam element is manually rotated. In variations of any embodiment the détente mechanism includes a pin urged toward a cam with a recess for receiving the pin. In variations of any embodiment the détente mechanism includes stops that allow the cam element to rotate a predefined position beyond a position of the bosses so as to releasably trap the cam element in a selected position. In variations of any embodiment a retaining element holds two of the tubing branches 1 and 3 in a crossing relation such that each of tubing branches 1 and 3 is positioned closer to a respective one of two others 2 and 4 than to each other (i.e., tubing branches 1 and 3 are more remote from each other than tubing branches 1 and 2 or tubing branches 3 and 4), thereby forming two paired adjacent tubing branches: pair 1=tubing branches 1 and 2 and pair 2=tubing branches 3 and 4 and such that each pair includes one of the crossing tubing branches, the cam element defining a flow path connecting flow branches 1 to 3 and 2 to 4 when in the first position and 1 to 4 and 2 to 3 when in the second position.

According to still more embodiments, the disclosed subject matter includes a flow switch device with a flow switch with four ports oriented at 90 degree intervals around a center of the flow switch. The flow switch is of a type that forms selectable flow passages between ports separated by 90 degrees and blocks flow between ports separated by 180 degrees in each of multiple selected positions. Two of the ports are connected to fixed flow passages each defining a flow path toward a remote port separated from the each by 180 degrees so that the each and a respective remote port are positioned in pairs on opposite sides of the flow switch. In variations of any embodiment the fixed flow passages include flexible curved tubes held by a retaining device to hold them in a curved state. In variations of any embodiment the retaining device includes a support that at least partially encloses the flow switch. In variations of any embodiment the retaining device includes a support that fully encloses the flow switch. In variations of any embodiment the retaining device is connected to the flow switch. In variations of any embodiment the flow switch has a manually operable actuator. In variations of any embodiment the retainer has indicia for indicates a position of the flow switch. In variations of any embodiment the retainer or the flow switch has indicia for indicates a position of the flow switch. In variations of any embodiment the retainer includes a flexible clip. In variations of any embodiment the retainer constitutes a flexible clip. In variations of any embodiment the each and the respective remote port have tubes extending parallel and away from the flow switch. In variations of any embodiment the each and the respective remote port have tubes extending parallel and in opposite directions from the flow switch.

It is, thus, apparent that there is provided, in accordance with the present disclosure, flow reversing device. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A flow switch device, comprising:
a port block having a rectangular cuboid shape and a central cavity, having a cylindrical shape, in the center of the port block, with four inner ports oriented at 90 degree intervals around an interior surface of the central cavity and four outer ports positioned on an outer surface of the port block, with each port of the four inner ports being in fluid communication with the central cavity and a corresponding one of the four outer ports, wherein a first of the outer ports and a second of the outer ports are positioned on a first outer face of the port block, and a third of the outer ports and a fourth of the outer ports are positioned on a second outer face of the port block, the second outer face being opposite to the first outer face; and a rotating element within the central cavity of the port block, the rotating element forming a seal with the port block and having two fixed flow passages, each of the two fixed flow passages having a curved shape and two ends such that when one end of a first fixed flow passage is aligned with a first one of the four inner ports, another end of the first fixed flow passage is aligned with a second one of the four inner ports that is oriented 90 degrees from the first one of the four inner ports, wherein the flow switch device forms selectable flow passages between pairs of the four inner ports separated from each other by 90 degrees and blocks flow between pairs of the four inner ports separated from each other by 180 degrees in each of multiple selected positions of the rotating element.

2. The flow switch device of claim 1, wherein the fixed flow passages connect, through the outer ports, to conduits that include flexible curved tubes held by a retainer to hold them in a curved state.

3. The flow switch device of claim 2, wherein the retainer includes a support that at least partially encloses the flow switch device.

4. The flow switch device of claim 2, wherein the retainer includes a support that fully encloses the flow switch device.

5. The flow switch device of claim 2, wherein the retainer is connected to the flow switch device.

6. The flow switch device of claim 2, wherein the flow switch device has a manually operable actuator.

7. The flow switch device of claim 6, wherein the retainer or the flow switch device has indicia for indicating a position of the flow switch device.

8. The flow reversing device of claim 1, wherein a first port, of two inner ports that are closest to the first outer face of the port block, fluidly connects to the first of the outer ports, a second port, of the two inner ports closest to the first outer face of the port block, fluidly connects to the third of the outer ports, a first port, of two inner ports closest to the second outer face of the port block, fluidly connects to the second of the outer ports, and a second port, of the two inner ports closest to the second outer face of the port block, fluidly connects to the fourth of the outer ports.

* * * * *